United States Patent [19]

Hetherington

[11] Plant 4,702

[45] Apr. 28, 1981

[54] ORCHID-LC. PUPPY LOVE-TRUE BEAUTY

[75] Inventor: Ernest E. Hetherington, Arcadia, Calif.

[73] Assignee: Fred A. Stewart Inc., San Gabriel, Calif.

[21] Appl. No.: 140,659

[22] Filed: Apr. 15, 1980

[51] Int. Cl.[3] ..... A01H 5/00
[52] U.S. Cl. ..... Plt./68
[58] Field of Search ..... Plt./68

*Primary Examiner*—Robert E. Bagwill
*Attorney, Agent, or Firm*—Edmond F. Shanahan

[57] ABSTRACT

A new and distinct variety of orchid, and more particularly a Laeliocattleya hybrid plant having flowers of a delicate clear pale lilac coloring. The new variety is distinctive from its parent population by its outstanding plant structure as well as its unusual coloring. The flowers are of exceptional substance (thicker and more resilient petals); they achieve perfect placement on the stem; the stem is superior in strength to the closest relatives; the flowers achieve longer bloom life; and the flower production is also superior to others of the same line of breeding.

2 Drawing Figures

DISCOVERY OF THE NEW VARIETY

The orchid of this application was discovered by the undersigned discoverer as an outstanding member of a large sibling population of the hybrid Laeliocattleya-Puppy Love (herein abreviated as Lc.-Puppy Love).

Prior to October, 1972, Lc.-Puppy Love had been developed in the orchid nursery of Fred A. Stewart, Inc., at San Gabriel, Calif., by crossing Cattleya Dubiosa 'Scullys' (pod parent), by Laelia anceps 'Barkeriana' (pollen parent). The resulting Lc.-Puppy Love was registered by the Stewart nursery with the Committee on Orchid Hybrid Registration of the Royal Horticultural Society, London, England, on Oct. 27, 1970; the new orchid was registered as "Stewart cross #1328 Lc.-Puppy Love".

In October, 1972, the new variety appeared as a single outstanding plant among a large population of Lc.-Puppy Love, all cultivated and blooming at Stewart's San Gabriel nursery. The plant of the new variety was immediately recognizable as superior in its flowers to all other members of the large population of the hybrid group Lc.-Puppy Love. After the new variety had been observed for a period of time, its other features of superior growth and structure were noted.

ASEXUAL REPRODUCTION

After its discovery in October, 1972, the original plant was placed in the laboratories of the Fred A. Stewart Inc. Nursery. During the years since 1972, a large number of plants of the new variety have been asexually produced by the meristem tissue method. Portions of tissue called meristem, comprised of unspecialized cells, capable of later differentiation, were cut from the plant, and developed, under carefully controlled sterile conditions, into new individual plants, which served, in turn, as additional sources of meristem tissue. The population thus produced has been carried under the Code Number SM-258.

All these propagations reproduced true to the original plant in both plant and flower, and in other characteristics. A substantial cross section has been flowered; they are exactly the same as the mother clone. All plants of the new variety have continued to be readily distinguishable from both parentage and all other siblings of the Lc.-Puppy Love hybrid population. The new variety has been designated Lc. Puppy Love-True Beauty.

DESCRIPTION OF THE PLANT

The plant and its flowers are illustrated in the color photographs accompanying this specification.

In some respects, the plant is typical of cattleya orchids; its strap leaves are coriacious, 20 cm. to 25 cm. long, and the plant attains a growth of 30 cm. to 30½ cm. on maturity. However, the plant develops a structure of superior and unusual strength and resiliency in its parts. The rhizome is short, branching often into flowering leads. The growth is compact and naturally erect; the plant has a stem and bifoliate leaves of superior strength. Its flowering habit is dependable, and proceeds from well-developed sheaths. The plants have been hardy in comparison with similar orchids. They have been virus and pathogen free during development, both in the original population of Lc.-Puppy Love, and in the meristem population of the new variety, Lc. Puppy Love-True Beauty. The cells have an even chromosome compliment. There are no characteristics of anuploidy or aberrant growth habit.

DESCRIPTION OF THE FLOWER

The outstanding merit of the new variety is the delicate coloring of the flower. Such coloring is difficult to obtain in the Laelia anceps line of breeding. The task is doubly difficult where larger size, better shape, and exceptional "keeping" qualities are desired, along with vigor and compactness of growth.

Both sepals and petals are mostly a pastel lilac, best identified by British Horticultural Colour Chart Page 437, Swatch Nos. 437-2 and 437-3. (Close horticultural examples are B.H.C.C. 437-1 Asystaia Bella, and 437 *Erigeron leiomerus.*) The texture of sepals and petals is sparkling and clear. The flowers hold their colors very well in comparison with their orchid relatives. The full and shapely labellum of the flowers is closed over the column, and is marginally the same color as the tepals (collective term for sepals and petals), shading throughout its central portions to B.H.C.C. No. 3-2, Aureolin (A close horticultural example is *Dendrobium speciosum*).

The flowers of the new variety are larger and stronger in structure than the average Laelia anceps hybrid.

The flowers average 12½ cm. in petal width. The new variety can carry as many as seven flowers on a mature, well grown plant. The flowers are perfectly carried on thin but strong erect flower spikes. Petals are flat and well carried, without twisting, turning, or recurving. The tepals are in symmetrical balance to the lip and create a good round shape to the flower as a whole.

The flowers last as long as four to five weeks, and are delicately fragrant throughout their life.

The blooming season is variable. However, years of observation have established that this variety has two distinct blooming seasons, one in midwinter, and one in summer. Three crops of flowers a year is not uncommon.

The above-described characteristics of the flowers of the new variety make them of superior value in the commercial cut flower market. The flowers preserve color and shape for a longer period of weeks than most similar orchids. They do not fade, spot, twist, or turn during that extended period.

I claim:

1. A new and distinct variety of orchid, of the hybrid genus Laeliocattleya, discovered as a superior variety of the grex Lc.-Puppy Love, and characterized by a combination of delicate lilac flower color and superior flower substance, i.e. strength of flower structure and stems; and further characterized by vigor, reliability of bloom, and exceptional lasting qualities.

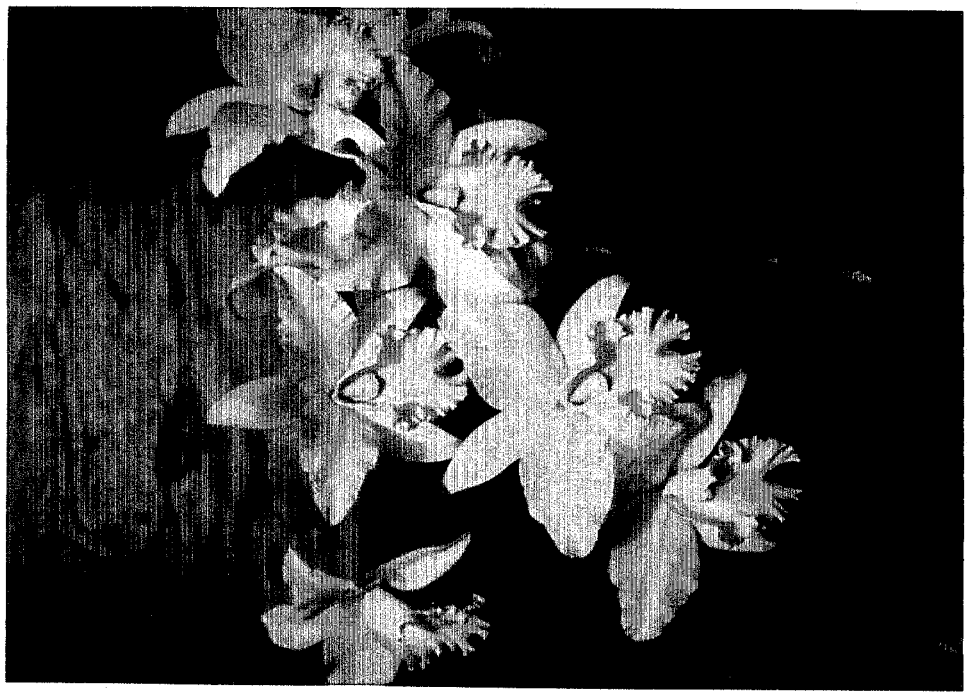
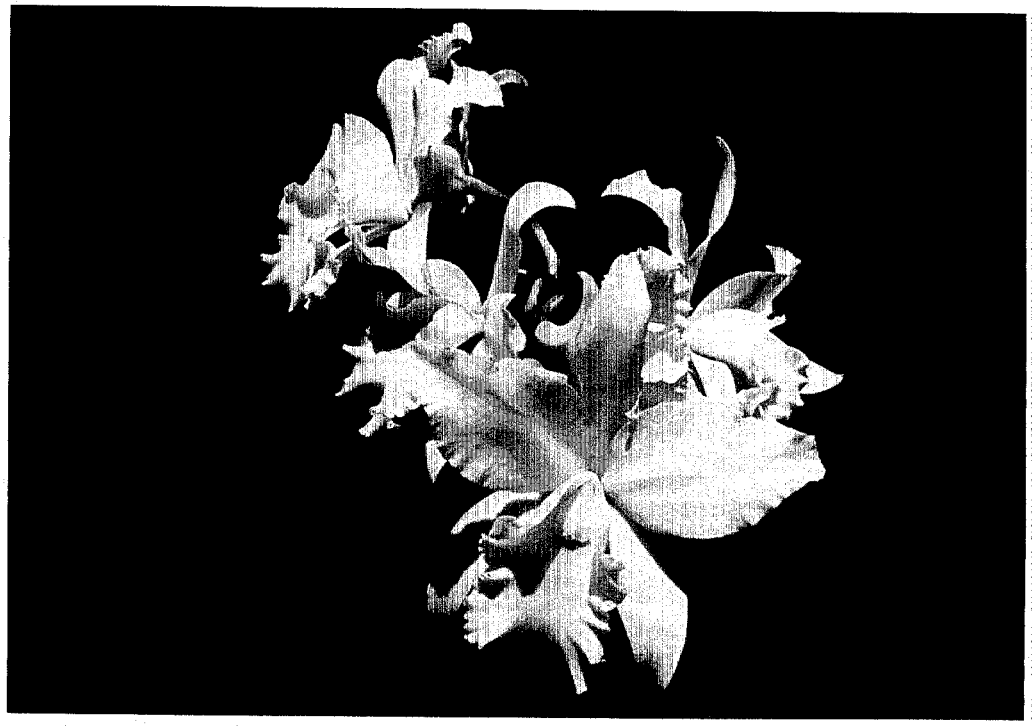

* * * * *